(12) United States Patent  
Sjostrom

(10) Patent No.: US 8,608,666 B2  
(45) Date of Patent: Dec. 17, 2013

(54) SURGICAL INSTRUMENT ASPIRATION VALVE

(75) Inventor: Douglas D. Sjostrom, Tewksbury, MA (US)

(73) Assignee: Smith & Nephew, Inc., Memphis, TN (US)

( * ) Notice: Subject to any disclaimer, the term of this patent is extended or adjusted under 35 U.S.C. 154(b) by 208 days.

(21) Appl. No.: 12/847,577

(22) Filed: Jul. 30, 2010

(65) Prior Publication Data

US 2010/0292675 A1  Nov. 18, 2010

Related U.S. Application Data

(62) Division of application No. 10/828,326, filed on Apr. 21, 2004, now abandoned.

(51) Int. Cl.
*A61B 5/00* (2006.01)

(52) U.S. Cl.
USPC .......................................................... 600/571

(58) Field of Classification Search
USPC ........................................ 600/562–572, 579
See application file for complete search history.

(56) References Cited

U.S. PATENT DOCUMENTS

| | | | |
|---|---|---|---|
| 1,952,617 | A | 3/1934 | Wappler |
| 3,815,604 | A | 6/1974 | O'Malley et al. |
| 3,828,780 | A | 8/1974 | Morrison, Jr. |
| 3,902,494 | A | 9/1975 | Haberlen |
| 3,945,375 | A | 3/1976 | Banko |
| 3,974,833 | A | 8/1976 | Durden, III |
| 4,203,444 | A | 5/1980 | Bonnell |
| 4,517,977 | A | 5/1985 | Frost |
| 4,522,206 | A | 6/1985 | Whipple et al. |
| 4,560,373 | A | 12/1985 | Sugino et al. |
| 4,655,197 | A | 4/1987 | Atkinson |

(Continued)

FOREIGN PATENT DOCUMENTS

| | | |
|---|---|---|
| EP | 0 791 336 | 8/1997 |
| JP | 02-232042 | 7/1989 |

(Continued)

OTHER PUBLICATIONS

PCT Application Serial No. PCT/US2005/013071, dated Aug. 19, 2005.

(Continued)

*Primary Examiner* — Max Hindenburg  
(74) *Attorney, Agent, or Firm* — Chapin IP Law, LLC

(57) ABSTRACT

A surgical instrument includes a movable member having a proximal portion, the movable member defining an opening at the proximal portion. The instrument includes a stationary member defining an aperture. The stationary member is arranged relative to the movable member with a close fit between the stationary member and the movable member such that aspiration occurs through the movable member substantially only during a portion of a repetitive motion of the movable member. The instrument includes a surgical handpiece coupled to the movable member and the stationary member to provide suction and motion to the movable member. A method of regulating aspiration through a surgical instrument includes providing a close fit between a moving member having an opening at a proximal portion and a stationary member having an aperture such that aspiration occurs through the moving member substantially only during a portion of a repetitive motion of the movable member. The moving member and the stationary member are coupled to a surgical handpiece to provide suction and motion to the moving member.

27 Claims, 11 Drawing Sheets

(56) References Cited

U.S. PATENT DOCUMENTS

| | | | |
|---|---|---|---|
| 4,662,371 | A | 5/1987 | Whipple et al. |
| 4,678,459 | A | 7/1987 | Onik et al. |
| 4,705,038 | A | 11/1987 | Sjostrom |
| 4,832,048 | A | 5/1989 | Cohen |
| 4,834,729 | A | 5/1989 | Sjostrom |
| 4,872,454 | A | 10/1989 | DeOliveira et al. |
| 4,955,882 | A | 9/1990 | Hakky |
| 4,957,482 | A | 9/1990 | Shiber |
| 4,983,179 | A | 1/1991 | Sjostrom |
| 5,006,114 | A | 4/1991 | Rogers et al. |
| 5,061,266 | A | 10/1991 | Hakky |
| 5,084,045 | A | 1/1992 | Helenowski |
| 5,102,410 | A | 4/1992 | Dressel |
| 5,112,330 | A | 5/1992 | Nishigaki et al. |
| 5,133,729 | A | 7/1992 | Sjostrom |
| 5,201,731 | A | 4/1993 | Hakky |
| RE34,556 | E | 3/1994 | Sjostrom |
| 5,300,069 | A | 4/1994 | Hunsberger et al. |
| 5,312,400 | A | 5/1994 | Bales |
| 5,314,406 | A | 5/1994 | Arias |
| 5,320,110 | A | 6/1994 | Wang |
| 5,334,140 | A | 8/1994 | Phillips |
| 5,335,671 | A * | 8/1994 | Clement ................ 600/566 |
| 5,441,503 | A | 8/1995 | Considine |
| 5,496,314 | A | 3/1996 | Eggers |
| 5,498,258 | A | 3/1996 | Hakky et al. |
| 5,505,210 | A | 4/1996 | Clement |
| 5,520,685 | A | 5/1996 | Wojciechowicz |
| 5,527,331 | A | 6/1996 | Kresch |
| 5,591,141 | A | 1/1997 | Nettekoven |
| 5,602,449 | A | 2/1997 | Krause et al. |
| D380,955 | S | 7/1997 | Landry |
| D381,425 | S | 7/1997 | Cesarini et al. |
| D388,170 | S | 12/1997 | Sjostrom |
| 5,697,927 | A | 12/1997 | Imran |
| 5,712,543 | A | 1/1998 | Sjostrom |
| D390,956 | S | 2/1998 | Sjostrom et al. |
| 5,749,885 | A | 5/1998 | Sjostrom |
| 5,814,044 | A | 9/1998 | Hooven |
| 5,871,493 | A | 2/1999 | Sjostrom et al. |
| 5,980,469 | A | 11/1999 | Burbank et al. |
| 6,090,122 | A | 7/2000 | Sjostrom |
| 6,152,941 | A | 11/2000 | Himes et al. |
| 6,312,441 | B1 | 11/2001 | Deng |
| 6,328,752 | B1 | 12/2001 | Sjostrom |
| 6,387,056 | B1 * | 5/2002 | Kieturakis ................ 600/565 |
| 6,436,067 | B1 | 8/2002 | Deng et al. |
| 7,226,459 | B2 | 6/2007 | Cesarini et al. |
| 7,510,563 | B2 | 3/2009 | Cesarini et al. |
| 7,766,844 | B2 * | 8/2010 | Sjostrom ................ 600/571 |
| 2002/0120212 | A1 | 8/2002 | Ritchart et al. |

FOREIGN PATENT DOCUMENTS

| | | |
|---|---|---|
| JP | 2000507840 | 6/2000 |
| WO | 95/10981 | 4/1995 |
| WO | 96/11638 | 4/1996 |
| WO | 96/24296 | 8/1996 |
| WO | WO9716124 A1 | 5/1997 |
| WO | 03/022164 A1 | 3/2003 |
| WO | WO03037194 A1 | 5/2003 |

OTHER PUBLICATIONS

Office action for Japanese Patent Application No. 2007-509539 corresponding to PCT/US2005/013071 mailed Jul. 21, 2011.

* cited by examiner

ND ASPIRATION# SURGICAL INSTRUMENT ASPIRATION VALVE

CROSS-REFERENCE TO RELATED APPLICATIONS

This application is a divisional of U.S. application Ser. No. 10/828,236, filed Apr. 21, 2004, and titled "SURGICAL INSTRUMENT ASPIRATION VALVE". The contents of the prior application are incorporated by reference herein in their entirety.

TECHNICAL FIELD

This disclosure relates to a surgical instrument aspiration valve.

BACKGROUND

Referring to FIGS. 1 and 2, a prior art surgical instrument is shown that is used to resect tissue using a tube-in-tube construction that shears tissue disposed between cutting edges of an outer non-rotating tube 370 and an inner rotating shaft 374 of a rotary cutter 300, as more fully explained in U.S. Pat. No. 5,871,493, which is incorporated herein by reference in its entirety. Outer tube 370 is connected to a hub 320 at a proximal region 371 of outer tube 370, and inner shaft 374 is rotatably received in hub 320 and outer tube 370. Inner shaft 374 includes a tube 376 located within outer tube 370. Tube 376 defines an aspiration lumen 378 and connects to a motor coupling 350 located in a proximal region of shaft 374 and partially received within hub 320. Motor coupling 350 includes an extension 355 coupled to a drive mechanism 115 that rotates shaft 374 relative to hub 320 and outer tube 370. Hub 320 includes a coupling in the form of a resilient latching mechanism 310 for connecting rotary cutter 300 to a handpiece 100, as discussed in U.S. Pat. No. 5,871,493. In particular, mechanism 310 includes a cantilevered resilient arm 315 with ramped latches 330 that engage an annular flange 610 in handpiece 100 to axially secure rotary cutter 300 to handpiece 100 as shown in FIG. 7B of U.S. Pat. No. 5,871,493. Other embodiments of the latching mechanism are also described in U.S. Pat. No. 5,871,493.

Handpiece 100 (FIG. 2) includes an aspiration channel 630 terminating at an aspiration opening 633 for applying suction to aspiration lumen 378 to remove fluid and cut tissue from a surgical site. Aspiration lumen 378 in tube 376 of shaft 374 has a proximal opening 375 that communicates with a through hole 380 in motor coupling 350. Suction is applied through aspiration channel 630 to draw material through a side-facing window 305 in outer tube 370 and a side-facing window 307 in inner tube 376, into lumen 378, and through lumen opening 375 and both ends of hole 380 to aspiration channel 630.

SUMMARY

In the surgical instrument of prior art FIGS. 1 and 2, the through hole 380 in the motor coupling 350 is in communication with the aspiration channel 630 when rotary cutter 300 is inserted into handpiece 100 regardless of the rotational position of through hole 380 due to the clearance between motor coupling 350 and an inner wall 622 of handpiece 100. However, due to the intermittent overlay of outer tube window 305 over inner tube window 307, automatic regulation of aspiration is provided since aspiration occurs through inner tube 376 substantially only when the windows are at least partially aligned. Since aspiration is not continuous, potential problems associated with excess fluid removal from the surgical site are generally not encountered.

Surgical instruments with distal end configurations that differ from the side cutter described above, for example, cutting blades such as open ended burrs and linearly reciprocating cutters, which are always, or almost always, open to the surgical environment, do not automatically regulate aspiration.

According to one aspect, a surgical instrument hub includes a body having a wall defining a channel for receiving a moving member. The wall defines an aperture configured to change a level of fluid communication with an opening in the moving member as the moving member moves. The body includes a coupling configured to connect the body to a handle.

Embodiments of this aspect may include one or more of the following features.

The aperture is configured to intermittently overlay the opening in the moving member. The aperture is in fluid communication with the channel. The wall defines a second aperture. The coupling includes a resilient member for connecting the hub to the handpiece. At least a portion of the wall surrounding the aperture has a beveled edge.

According to another aspect, a surgical instrument includes a shaft defining an opening in a proximal region of the shaft, and a hub defining an aperture configured to change a level of fluid communication with the opening as the shaft moves.

Embodiments of this aspect may include one or more of the following features.

The aperture is configured to intermittently overlay the opening as the shaft moves. The hub has a wall defining a channel for receiving the shaft. The hub includes a coupling configured to connect the hub to a handle. The shaft defines a lumen in fluid communication with the opening. The shaft includes a distal opening in fluid communication with the shaft lumen. The surgical instrument includes an outer tube surrounding the shaft and connected to the hub, and a handle connected to the hub.

According to another aspect, a method includes suctioning fluid through a lumen of a surgical instrument, and automatically, intermittently, substantially closing off an opening in fluid communication with the lumen at a proximal region of the lumen to limit fluid aspiration.

Embodiments of this aspect may include one or more of the following features.

The opening is in a shaft of the surgical instrument, and automatically, intermittently, substantially closing off the opening includes moving the shaft relative to a hub of the surgical instrument such that an aperture in the hub is intermittently out of alignment with the opening. Moving the shaft includes, e.g., rotating the shaft, reciprocating the shaft, or oscillating the shaft. The shaft defines a second opening and rotating the shaft causes the aperture to be intermittently out of alignment with the second opening.

According to another aspect, a method of regulating aspiration through a surgical instrument includes providing a close fit between a moving member having an opening at a proximal portion and a stationary member having an aperture such that aspiration occurs through the moving member substantially only during a portion of a repetitive motion of the movable member. The moving member and the stationary member are coupled to a surgical handpiece to provide suction and motion to the moving member. Embodiments of this aspect may include one or more of the following features. During the portion of the repetitive motion of the movable member the aperture at least partially overlays the opening.

According to another aspect, a surgical instrument includes a movable member having a proximal portion, and the movable member defines an opening at the proximal portion. The instrument includes a stationary member defining an aperture. The stationary member is arranged relative to the movable member with a close fit between the stationary member and the movable member such that aspiration occurs through the movable member substantially only during a portion of a repetitive motion of the movable member. The instrument includes a surgical handpiece coupled to the movable member and the stationary member to provide suction and motion to the movable member.

Embodiments of this aspect may include one or more of the following features.

The stationary member is arranged relative to the movable member such that the aperture intermittently overlays the opening during the portion of the repetitive motion of the movable member. The stationary member includes a hub defining the aperture, and the hub includes a coupling configured to connect to the surgical handpiece.

The surgical instrument with, for example, the close fit between the moving member and the stationary member in the region where suction is applied to the members addresses the problem of excess fluid usage. The reduction in fluid usage is achieved without reducing a diameter of the surgical instrument, which can cause clogging. The surgical instrument is particularly applicable for use in environments where it is not practical to increase the fluid volume at the surgical site to compensate for fluid removal, such as transcervical intrauterine fibroid resection, and where excess fluid removal could cause collapse of the surgical environment, such as intra-articular closed surgery, such as of the knee.

The details of one or more embodiments are set forth in the accompanying drawings and the description below. Other features will be apparent from the description and drawings, and from the claims.

DETAILED DESCRIPTION

Figure 3:
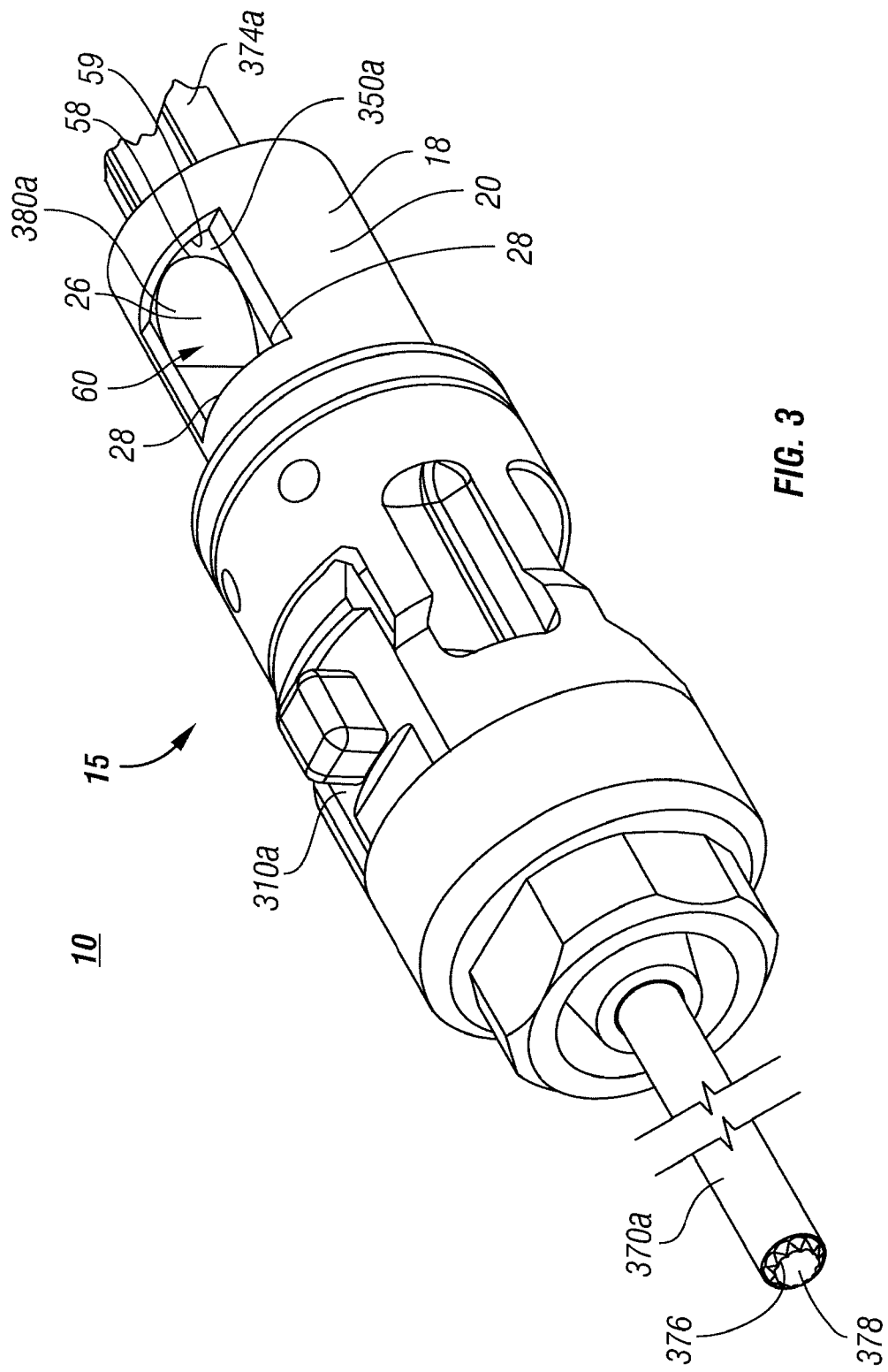
FIG. 3 is a perspective view of a surgical cutter including a hub according to the invention.
Figure 4:
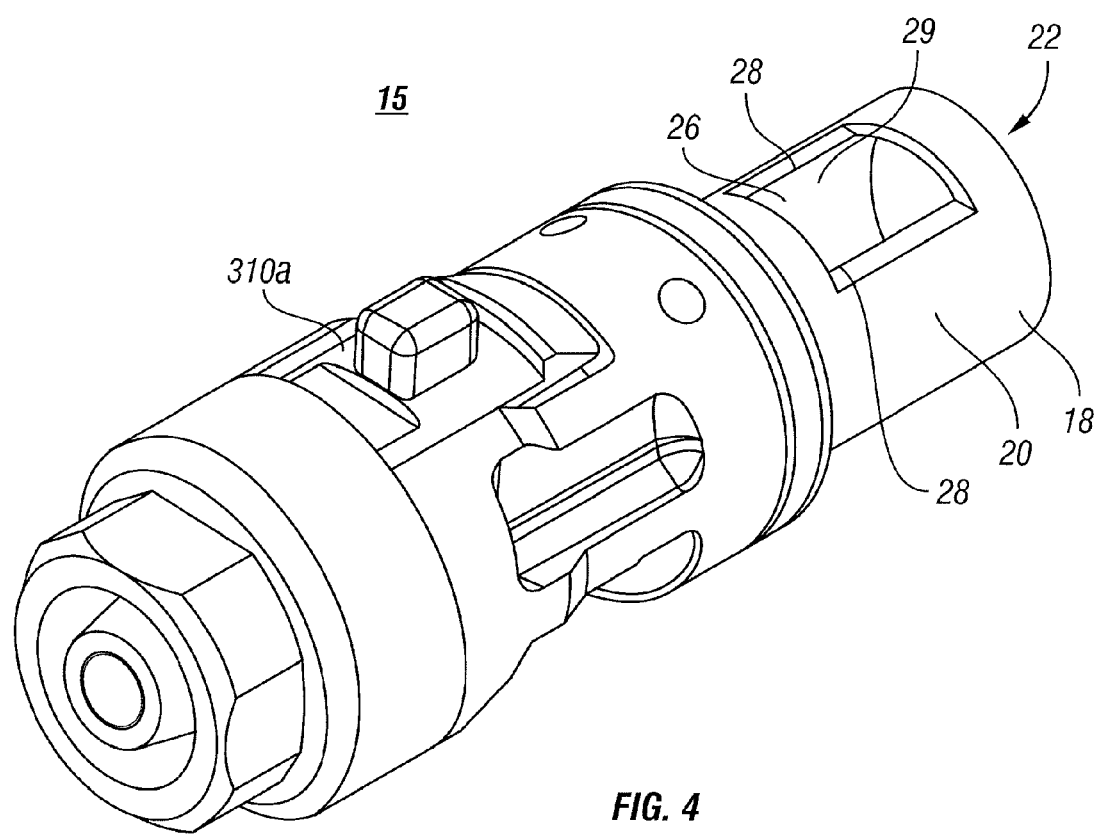
FIG. 4 is a perspective view of the hub of FIG. 3.

Referring to FIGS. 3 and 4, a rotary cutter 10, for example, an open ended burr cutter, includes an outer tube 370a and an inner shaft 374a, as described above with respect to FIG. 1 except for the different type of distal cutter. Outer tube 370a is coupled to a hub 15 having a resilient latching mechanism 310a, as described above with respect to latching mechanism 310, for connecting cutter 10 to handpiece 100. Hub 15 is substantially as described above with reference to hub 320, with the addition of a proximally extending body 18 having a wall 20 defining a longitudinal channel 22 and an aperture 26 extending through wall 20 and in fluid communication with channel 22.

Aperture 26 is positioned over a motor coupling 350a of shaft 374a in the region of a side hole 380a of motor coupling 350a such that, as shaft 374a rotates relative to hub 15, aperture 26 intermittently overlays side hole 380a to form an aspiration valve 60. Side hole 380a extends only partially through motor coupling 350a, as opposed to through hole 380 of FIG. 1. Aperture 26 is defined in part by side edges 28 of wall 20. Side edges 28 are beveled to cut tissue in the event that tissue becomes lodged in aperture 26. An edge 58 that defines side hole 380a in motor coupling 350a is sharp so as to cooperate with side edges 28 in shearing tissue. Edge 58 need not be sharp at locations on edge 58 that do not cut tissue.

Figure 5:
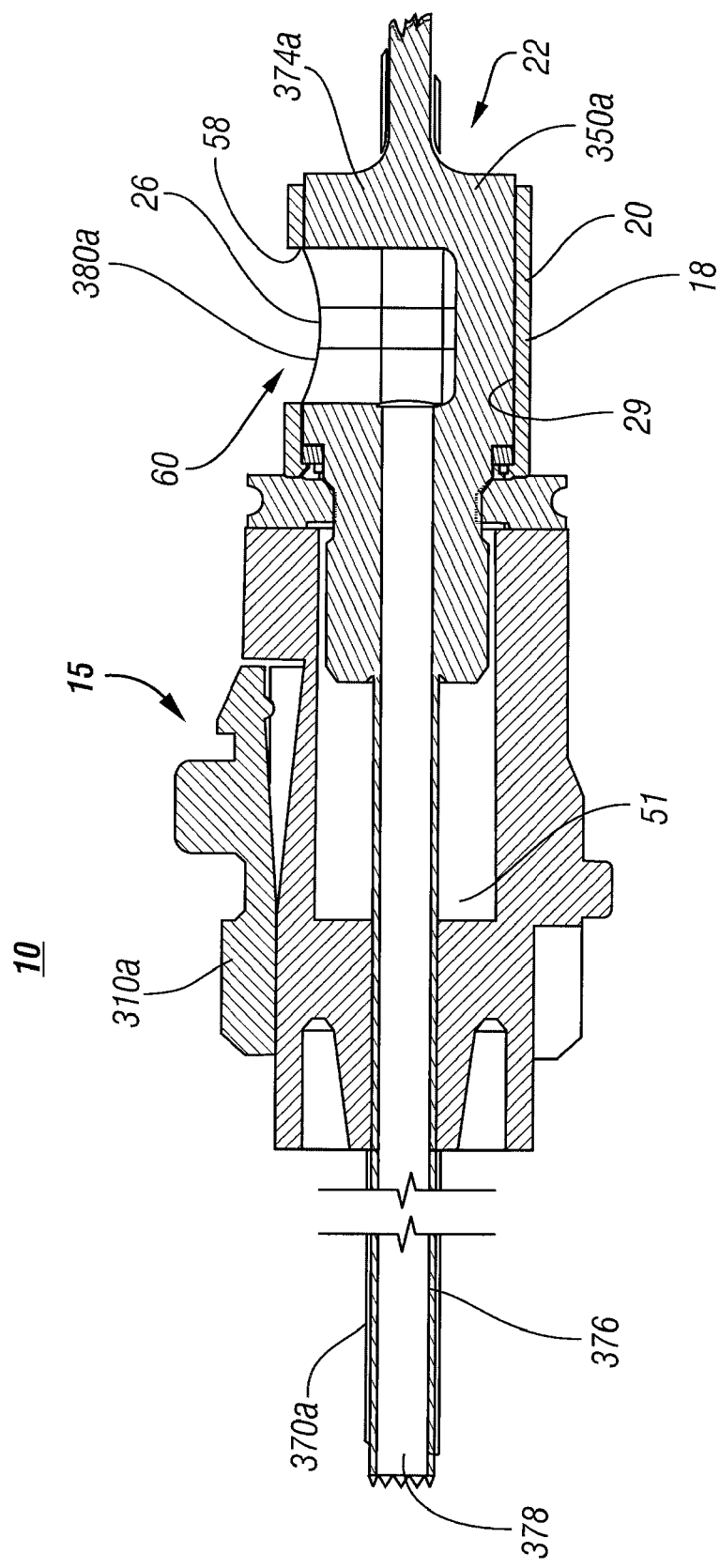
FIG. 5 is a longitudinal cross-sectional view of the surgical cutter of FIG. 3 shown with an opening in the hub overlaying an opening in a shaft of the surgical cutter.
Figure 6:
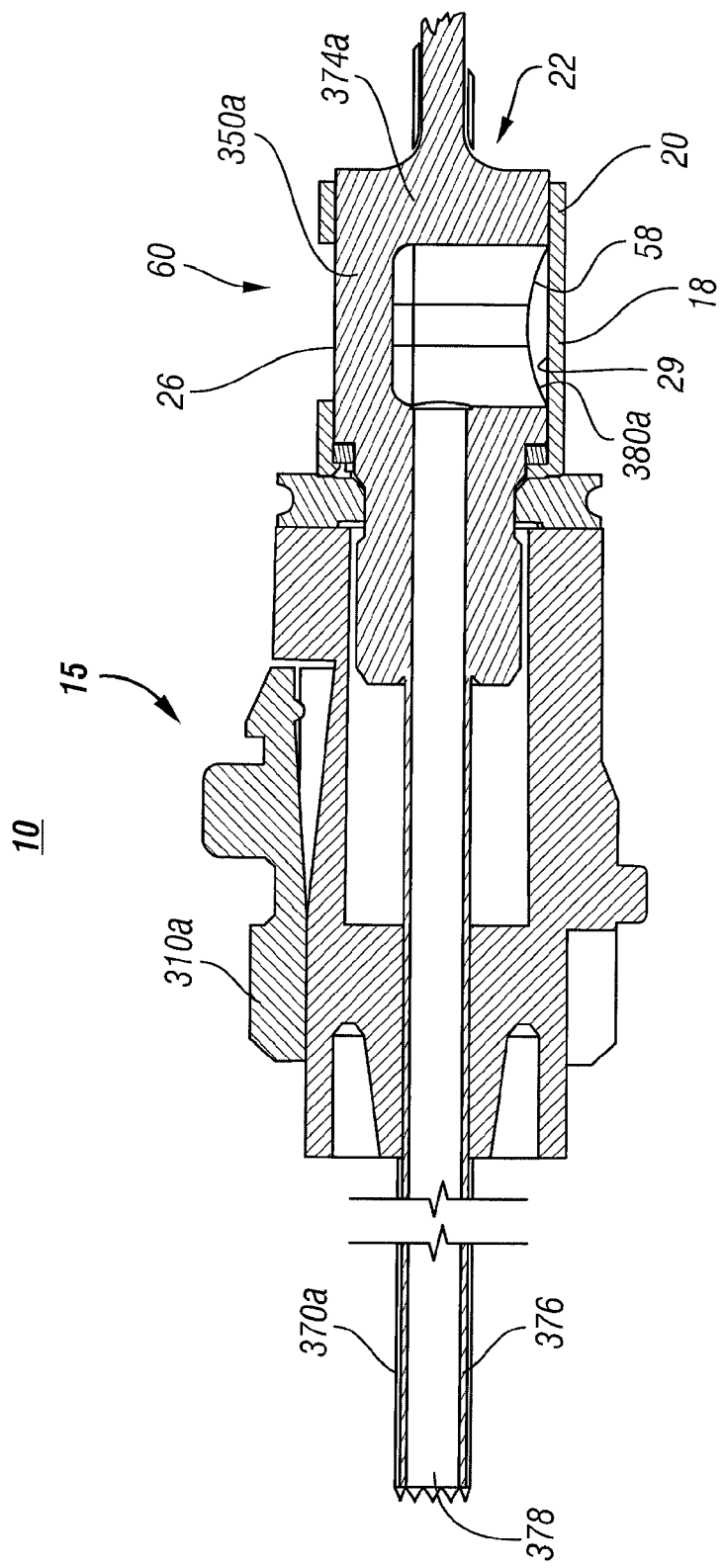
FIG. 6 is a longitudinal cross-sectional view of the surgical cutter of FIG. 3 shown the shaft rotated relative to FIG. 5.

Referring to FIG. 5, during a portion of the rotation of shaft 374a, aperture 26 overlays side hole 380a such that part or all of side hole 380a is exposed through aperture 26, permitting the application of suction to inner tube lumen 378. FIG. 6 shows shaft 374a rotated 180 degrees relative to FIG. 5, such that aperture 26 does not overlay side hole 380a. Body 18 surrounds motor coupling 350a such that when aperture 26 does not overlay side hole 380a, side hole 380a is essentially blocked by an interior surface 29 of wall 20 limiting the application of suction to inner tube lumen 378. In particular embodiments, the clearance between an exterior surface 59 of motor coupling 350a and interior surface 29 of wall 20 falls within a range of approximately 0.001 inches to approximately 0.010 inches, preferably approximately 0.001 inches to approximately 0.005 inches, and most preferably approximately 0.001 inches to approximately 0.002 inches to provide a close fit between motor coupling 350a and wall 20 such that aspiration valve 60 is formed that limits the application of suction to, and thus the removal of fluid through, tube 376.

Other embodiments may use a larger or smaller clearance depending on a variety of factors. One such factor is whether the surgical instrument is side-loaded, such as, for example, side opening rotary cutter 300 of FIG. 1, which can experience lateral displacement of a motor coupling and can require greater clearance to maintain low friction. Other factors include, for example, (i) aspiration fluid rate, with a higher fluid rate possibly allowing a greater clearance and greater leakage and still providing sufficient restriction of aspiration, and (ii) the diameter of the tubes being used, for embodiments using tubes, with larger diameters possibly providing a greater fluid rate and therefore tolerating a greater clearance. Excessive clearance can contribute to clogging and annular leakage around exterior surface 59. To minimize annular leakage, a seal can be provided and can be particularly useful with large clearances.

Thus, aperture 26 and side hole 380a form aspiration valve 60 for automatically regulating the application of suction through cutter 10. The operation of valve 60 restricts aspiration through cutter 10 without, for example, decreasing the diameter of inner tube 376 or requiring an operator to manually open and close a valve. The intermittent application of suction restricts aspiration through cutter 10 while shaft 374a rotates. Aspiration can also be restricted when shaft 374a is stationary by stopping rotation of shaft 374a when shaft 374a is positioned with side hole 380a out of alignment with aperture 26. Such a stopping mechanism is described in U.S. Pat. No. 5,602,449, hereby incorporated by reference in its entirety.

Other embodiments are within the scope of the following claims.

Figure 7:
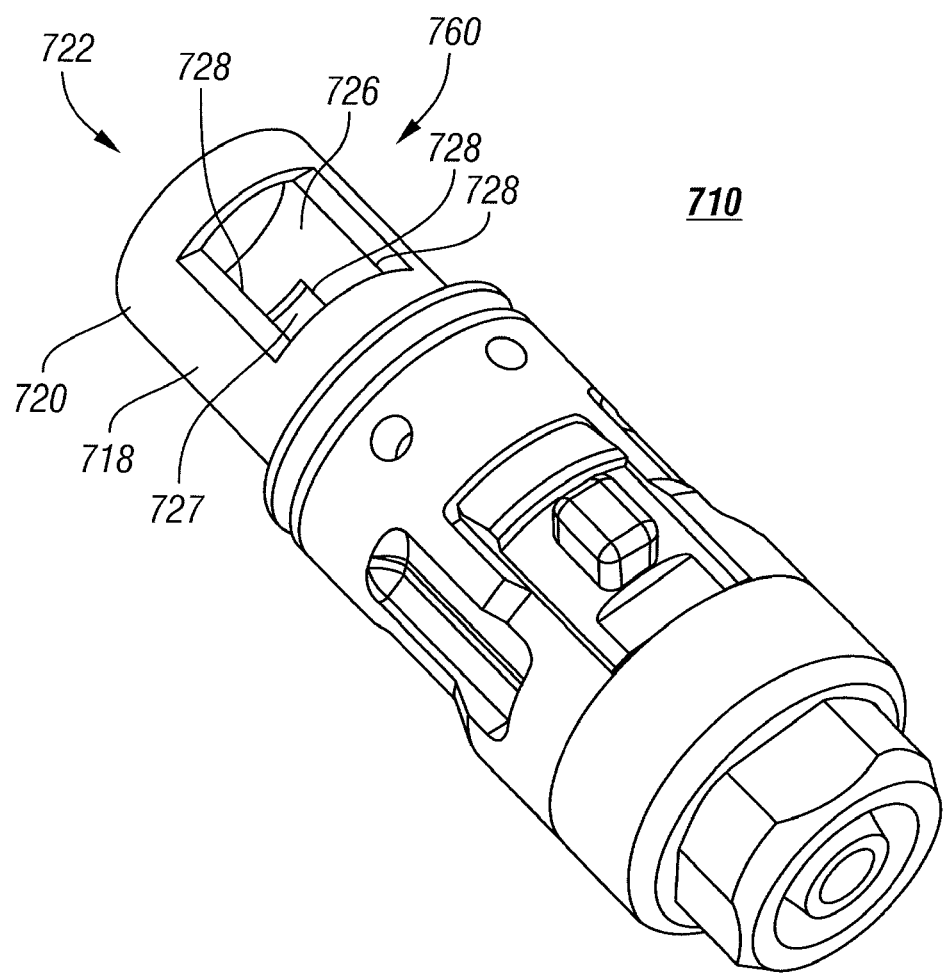
FIG. 7 is a perspective view of an alternative embodiment of a hub.

For example, referring to FIG. 7, a hub 710 includes a proximally extending body 718 having a wall 720 defining a longitudinal channel 722 and first and second apertures 726, 727 extending through wall 720 and in fluid communication with channel 722. Apertures 726 and 727 are defined in part by beveled edges 728 for cutting tissue. Suction is applied to inner tube lumen 378 when either of openings 726 or 727 overlays side hole 380a in motor coupling 350a, thus providing increased aspiration as compared to hub 15. Thus, openings 726 and 727, along with side hole 380a, form an aspiration valve 760 for automatically regulating suction.

Figure 8:
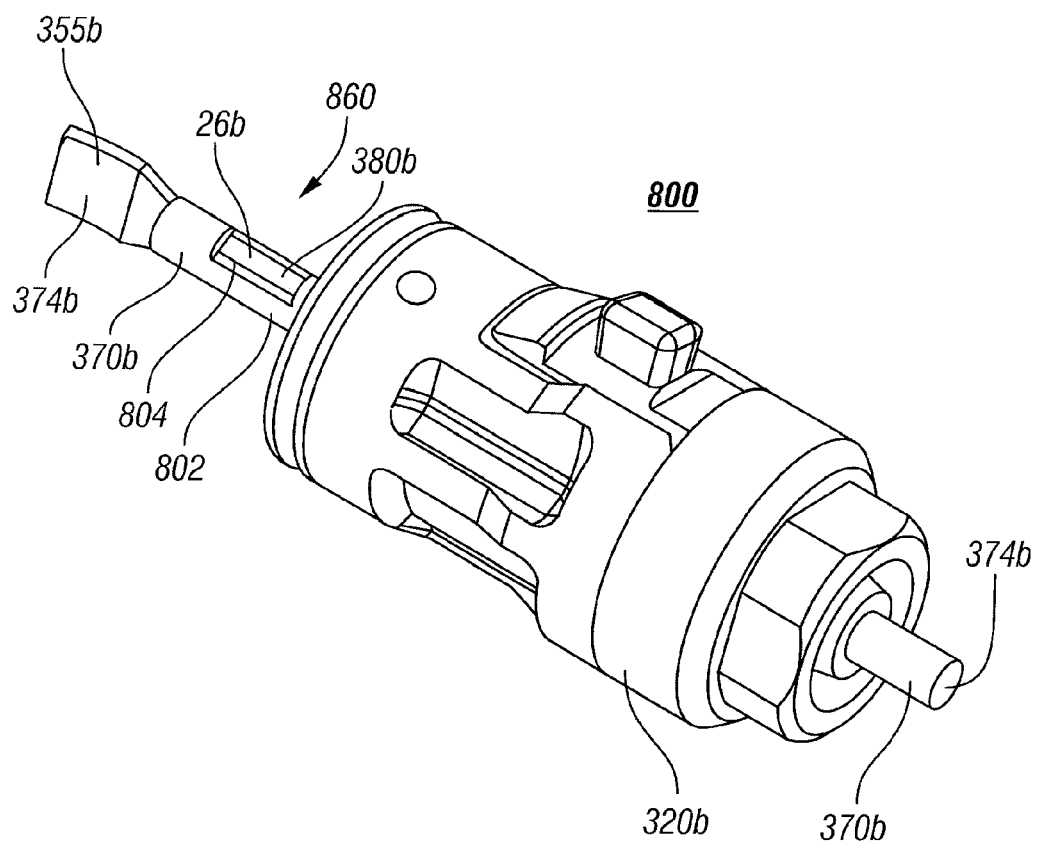
FIG. 8 is a perspective view of an alternative embodiment of a cutter.

In other embodiments, structure other than a hub is used to restrict aspiration. For example, referring to FIG. 8, a rotary cutter 800 includes a stationary outer tube 370b having a proximal portion 802 that defines an aperture 26b. Cutter 800 also includes a rotating inner shaft 374b having a proximal portion 804 that defines a side hole 380b. Shaft 374b has a proximal extension 355b for cooperating with a drive mechanism such as, for example, drive mechanism 115. Cutter 800 further includes a hub 320b through which tube 370b and shaft 374b extend. Stationary outer tube 370b is fixedly attached to hub 320b, for example, by using glue, using epoxy, welding, or overmolding, and hub 320b connects to a handpiece such as, for example, handpiece 100. Hub 320b is substantially similar to hub 320 of FIG. 1. Proximal portion 802 of tube 370b operates in a manner similar to body 20 of hub 15 of FIG. 3, with aperture 26b and side hole 380b forming an aspiration valve 860 for automatically regulating the application of suction through cutter 800.

Aspiration valve 860 has a smaller diameter than, for example, aspiration valves 60 or 760. Because of the smaller diameter, less power is required in order to cut tissue that may become lodged in valve 860 as valve 860 closes. Because of the smaller diameter, there is also less surface area available for contact between tube 370b and shaft 374b in the vicinity of valve 860 than, for example, between wall 20 and motor coupling 350a of shaft 374a in the vicinity of valve 60, and the reduced surface area produces a reduced amount of friction which requires less power to overcome. The reduced friction also can mitigate some of the effects of lateral displacement in side-loaded embodiments, as discussed earlier. To further mitigate the effects of lateral displacement in a side-loaded embodiment, aperture 26b and side hole 380b can be moved distally toward a point (see, e.g., a connection point 51 in FIG. 5) where tube 370b is attached to hub 320b.

Figure 1:
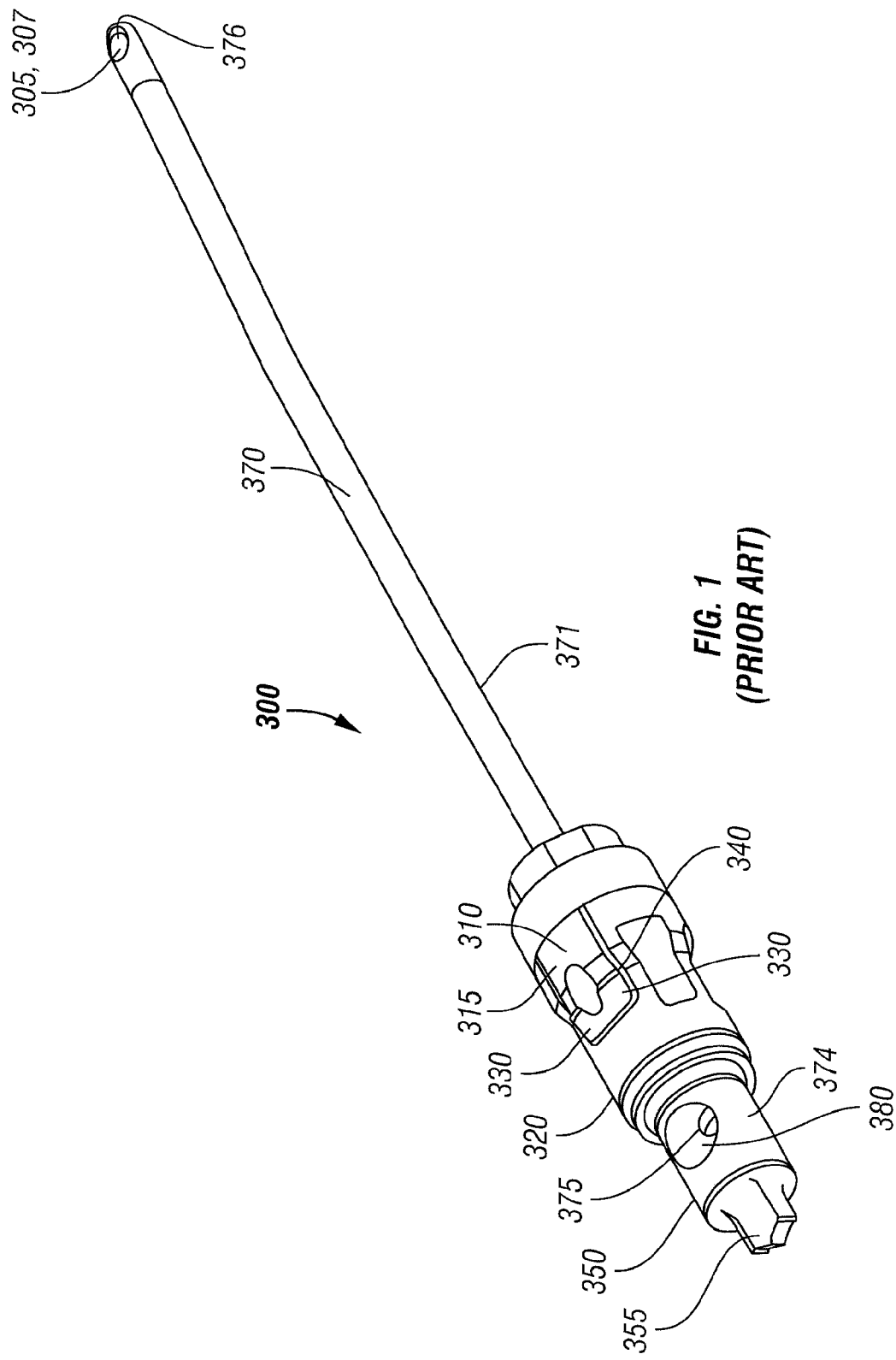
FIG. 1 is a perspective view of a prior art rotary cutter.
Figure 2:
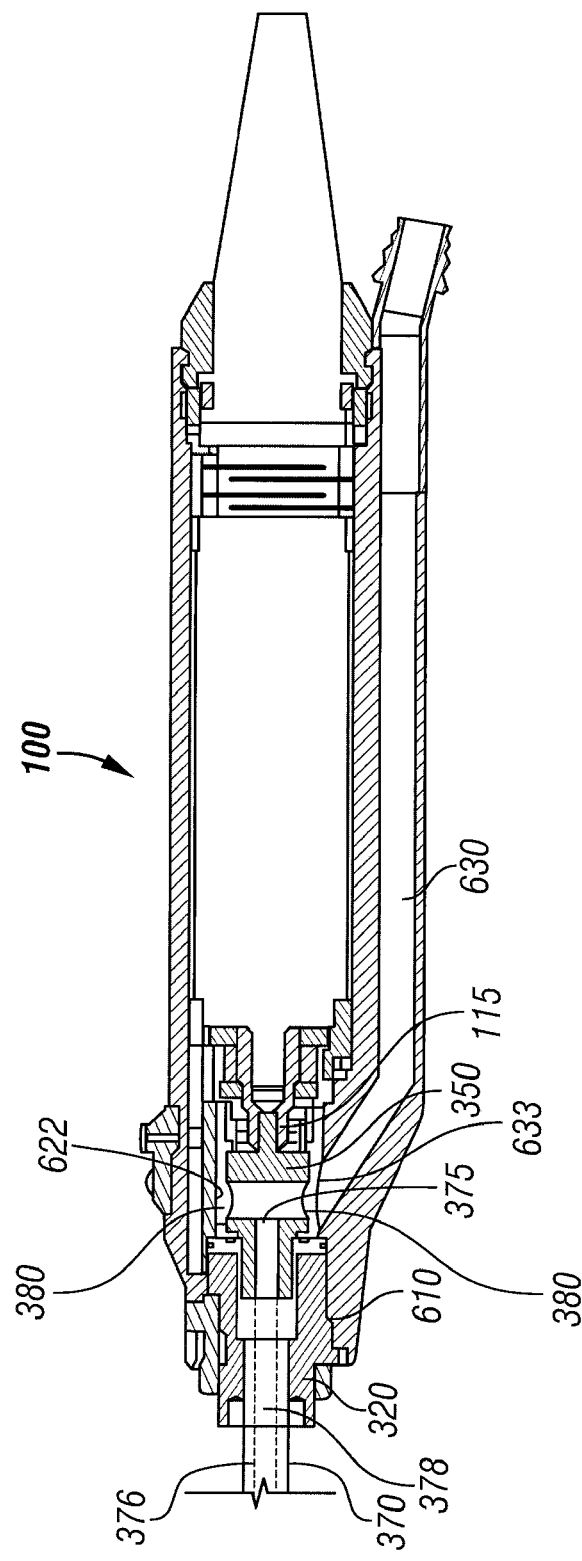
FIG. 2 is a cross-sectional view of a hub of the prior art rotary cutter of FIG. 1 coupled to a handpiece.

Another embodiment that uses structure other than a hub to restrict aspiration is achieved by reducing the clearance between motor coupling 350 and inner wall 622 of FIGS. 1 and 2. By reducing the clearance, for example, as described above with respect to the clearance between exterior surface 59 of motor coupling 350a and interior surface 29 of wall 20, an aspiration valve is formed by aspiration opening 633 and through hole 380 for automatically regulating the application of suction.

Figure 9:
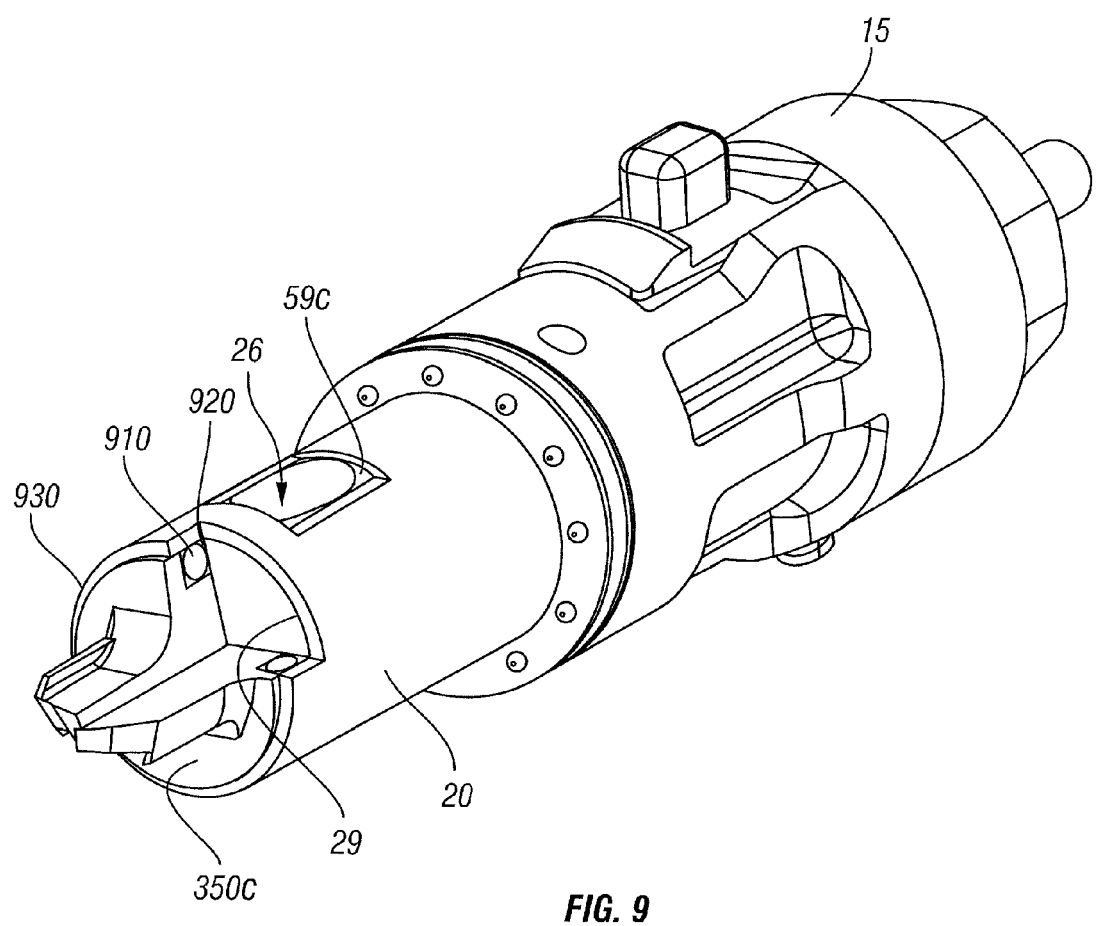
FIG. 9 is a perspective view of an embodiment with a seal, the view including a cut-away showing the seal.

Referring to FIG. 9, a motor coupling 350c includes a seal 910, for example, an O-ring. Seal 910 is positioned in a cavity 920 in motor coupling 350c, which is otherwise similar to motor coupling 350a. Seal 910 provides a sealing function between motor coupling 350c and hub 15. Specifically, seal 910 provides a sealing function between interior surface 29 of wall 20 and exterior surface 59c of motor coupling 350c. When a vacuum source is coupled to motor coupling 350c, the source generally applies suction to a proximal end 930 of wall 20 as well as to the intended aspiration path through opening 26. Seal 910 restricts annular leakage from proximal end 930 between wall 20 and motor coupling 350c, thus reducing fluid aspiration. Other embodiments can use a seal in additional or alternative locations, depending on the particular application, to restrict leakage.

Figure 10:
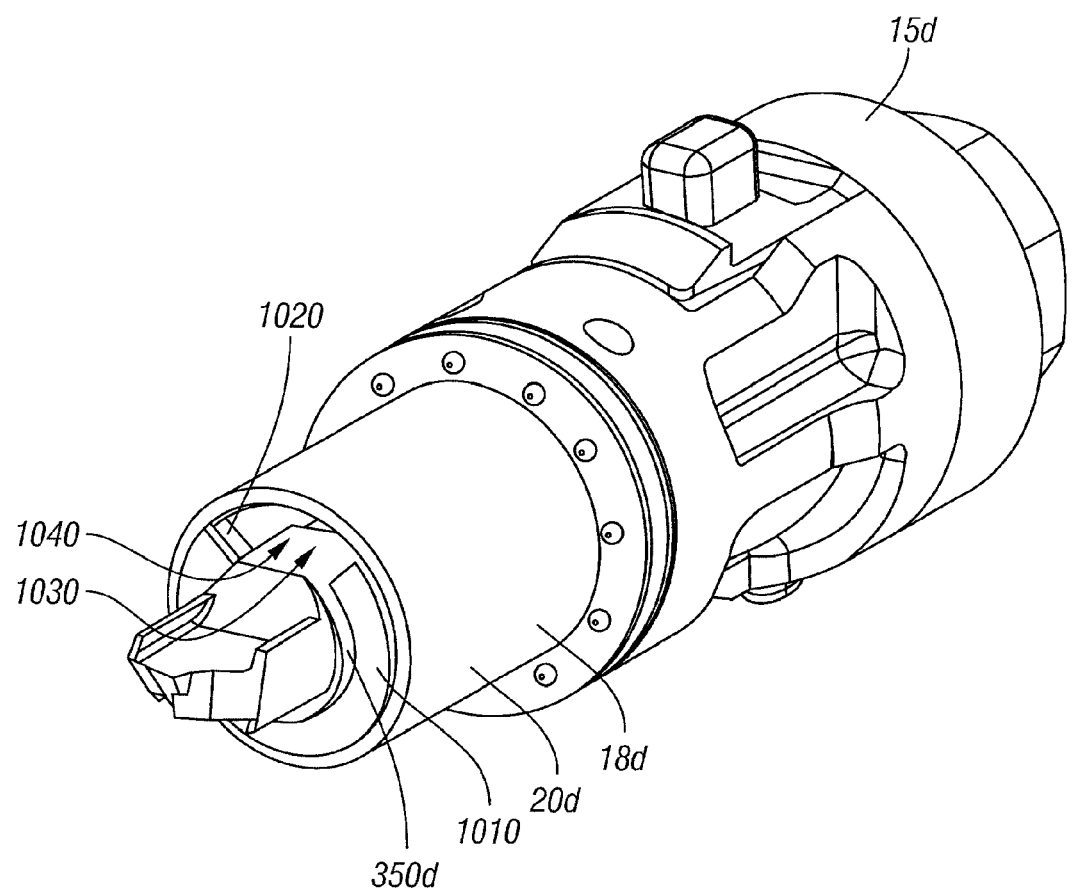
FIG. 10 is a perspective view of an embodiment with two flanges, showing complete overlay.
Figure 11:
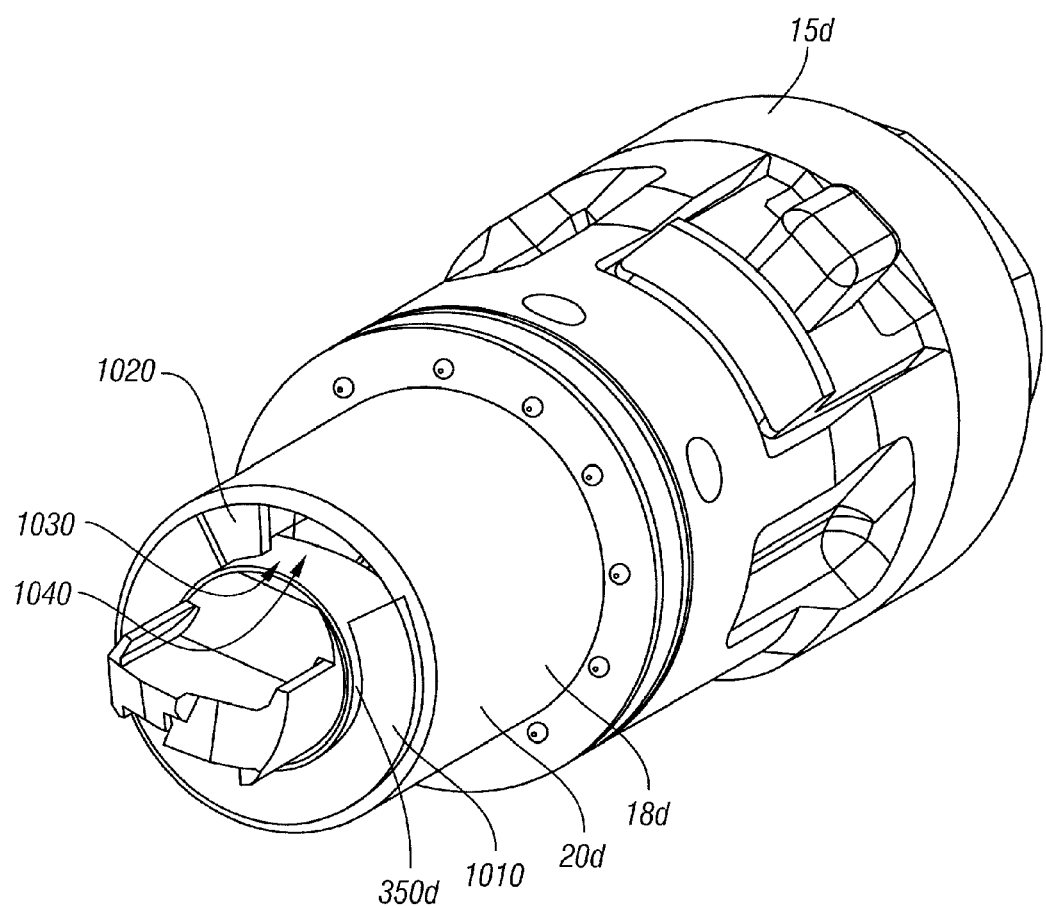
FIG. 11 is a perspective view of an embodiment with two flanges, showing partial overlay.

Referring to FIGS. 10 and 11, a motor coupling 350d includes a partially circular coupling flange 1010 that cooperates with a partially circular body flange 1020 of a body 18d of a hub 15d to regulate aspiration. Coupling flange 1010 and body flange 1020 are positioned longitudinally adjacent to one another. Coupling flange 1010 defines a coupling opening 1030, and body flange 1020 defines a body opening, or aperture, 1040. Coupling flange 1010 rotates with motor coupling 350d such that as motor coupling 350d rotates, coupling opening 1030 intermittently overlays, and is in fluid communication with, stationary body opening 1040 to provide a path for aspiration. FIG. 10 shows coupling opening 1030 completely overlaying body opening 1040, whereas FIG. 11 shows coupling opening 1030 only partially overlaying body opening 1040. Motor coupling 350d includes a side hole (not shown), such as side hole 380a (FIG. 3), that is aligned longitudinally with coupling opening 1030. Other embodiments can have the side hole moved with respect to coupling opening 1030. Flanges 1010 and 1020 can form a liquid-tight seal, or can allow some leakage. Even if leakage occurs, however, the intermittent overlaying of openings 1030 and 1040 provides increased fluid communication between openings 1030 and 1040 when openings 1030 and 1040 are aligned.

Another embodiment provides a stationary member that can be repositioned with respect to a hub. For example, one such embodiment is formed by modifying hub 15 of FIG. 3 so that body 18 can be moved with respect to the rest of the hub. The movable body can be, for example, rotated around a longitudinal axis of the hub. The movable body can be locked in a particular rotational position by, for example, using a system of detents, and the actual rotational position can be indicated by, for example, using a set of markings, such as an index, on the movable body and/or the hub. Such rotational motion allows an aperture, similar to aperture 26 of FIG. 3, to be, for example, positioned at different rotational positions to adjust alignment with aspiration channel 630. Adjusting the alignment of the aperture can include reducing alignment with the aspiration channel so as to restrict aspiration, or increasing alignment so as to increase aspiration. One embodiment uses a hub that can connect to a handpiece in more than one position, and the movable body allows the aperture in the movable body to be aligned with an aspiration channel of the handpiece regardless of which position the hub is in with respect to the handpiece.

The operation of an aspiration valve, such as, for example, valves 60, 760, and 860, has been described above in which an opening in the movable member and an aperture in the stationary member are configured such that the aperture and the opening are in fluid communication during a portion of the repetitive motion of the movable member. Fluid communication can be achieved, as in valves 60, 760, and 860, by overlaying the aperture and the opening. Overlaying can be achieved, as in rotary valves 60, 760, and 860, by virtue of a rotating motion of the movable member which intermittently brings the aperture and the opening into alignment such that the aperture intermittently overlays the opening. The rotating motions can be in a single rotational direction or can oscillate back and forth in different rotational directions. Further, the movable member of the valve can undergo other types of motions to restrict aspiration, such as, for example, a back-and-forth linear motion along a longitudinal axis of the surgical instrument, referred to as a reciprocating motion. Additionally or alternatively, the valve can be formed without the use of a stationary member by, for example, using an opening in a first movable member and an aperture in a second movable member. Valves 60, 760, 860 can be used to restrict or regulate suction of various types of instruments, including, for example, instruments that use a rotating motion or a reciprocating motion.

Embodiments can be used with side-cutting devices that already provide some aspiration regulation, as described above. Such embodiments can provide additional regulation of aspiration that can be of particular value, for example, in limiting aspiration when the side-cutting device's surgical windows (for example, windows 305 and 307 in FIG. 1) are open. The surgical windows can be open and the limited aspiration can be valuable while the movable window is, for example, either moving (for example, while window 307 in FIG. 1 is rotating) at a slow speed, or stopped. The location and timing of the valve, in relation to the surgical windows, can be varied depending on the application. Further, the openings of the valve can be, for example, smaller than the surgical windows and can provide additional cutting of aspirated tissue.

The embodiments described, and other embodiments, can regulate aspiration by, for example, operating such that the relative position of two openings is adjusted as a member moves to change the level, i.e., increase or reduce, of fluid communication between the openings, and thus the level of aspiration. An opening can be intermittently substantially closed off, and aspiration can occur substantially only during a portion of a repetitive motion. Some leakage will generally occur even when the openings are completely out of alignment due to the clearance between a movable member and a stationary member of a valve, and due to leakage between the movable member and the stationary member at their proximal ends, to which suction from aspiration channel 630 is also applied.

A number of embodiments have been described. Nevertheless, it will be understood that various modifications can be made. For example, the body of the hub can define a different number of apertures having any of various sizes and shapes, and the motor coupling can define a different number of openings, side holes or otherwise, having any of various sizes and shapes to vary the amount of applied suction. The aperture(s) in the body of the hub and/or the opening(s) in the motor coupling can be surrounded by a different number of sharpened edges or no sharp edges at all. The motor coupling can be coupled to various types of surgical instruments, such as, for example, a rotary burr, a reciprocating cutter, or a drill. The surgical instruments can operate using a variety of different motions, including, for example, rotation in a single direction, oscillation (rotation in alternating directions), reciprocation (longitudinal movement), or a combination of these motions. Latching mechanism 310*a* can employ any of the embodiments described in U.S. Pat. No. 5,871,493.

What is claimed is:

1. A surgical instrument hub, comprising:
   a body having a wall defining a channel for receiving a moving member, the moving member having a distal portion distal the body and configured and arranged to contact tissue, the wall defining an aperture that overlays an opening defined in a proximal portion of the moving member to define a valve configured to change a level of fluid communication between the aperture and the opening in the moving member as the moving member moves, the moving member switched between a first position and a second position to control flow from the distal portion through the aperture, the first position of the moving member aligning the opening of the moving member with the aperture of the wall to provide the flow from the distal portion through the aperture, the second position of the moving member blocking the aperture to prevent the flow from the distal portion through the aperture, the body including a coupling configured to connect the body to a handle.

2. The surgical instrument hub of claim 1 wherein the valve as operated in accordance with the first position and the second position is an aspiration valve, the aspiration valve providing discontinuous flow from the distal portion of the moving member through the aperture in the wall.

3. The surgical instrument hub of claim 2 wherein the aspiration valve is configured to control aspiration substantially only during a portion of a repetitive motion of the movable member.

4. The surgical instrument hub of claim 1 wherein the aperture is configured to intermittently overlay the opening in the moving member, the moving member providing discontinuous flow from the distal portion through a bore in the moving member and out the aperture in the wall.

5. The surgical instrument hub of claim 1 wherein the aperture is in fluid communication with the channel.

6. The surgical instrument hub of claim 1, wherein the aperture is a first aperture, the surgical instrument hub further comprising:
   a second aperture, the second aperture disposed on the wall opposite the first aperture; and
   wherein the opening in the moving member rotates about an axis, the opening in the moving member switching between aligning with the first aperture and the second aperture to provide discontinuous flow from the distal portion through a bore in the moving member and out the first aperture and second aperture.

7. The surgical instrument hub of claim 6, wherein rotation of the moving member about the axis shears tissue, disposed between a beveled edge on the first aperture.

8. The surgical instrument hub of claim 1 wherein at least a portion of the wall defining the aperture has a beveled edge; and
   wherein the moving member rotates about an axis, the axis extending between the distal portion and the proximal portion, rotation of the moving member about the axis shearing tissue disposed between the beveled edge and the opening of the moving member.

9. The surgical instrument hub of claim 8, wherein the moving member comprises a shaft, the shaft extending between the distal portion and the proximal portion, the shaft including an opening at the distal portion to receive the tissue, the tissue passing through a lumen in the shaft towards the aperture.

10. The surgical instrument hub of claim 9 wherein the aperture is configured to intermittently overlay the opening in the moving member as the shaft moves.

11. The surgical instrument hub of claim 9 wherein the wall defines a channel for receiving the shaft.

12. The surgical instrument hub of claim 9 further comprising an outer tube surrounding the shaft and connected to the surgical instrument hub.

13. The surgical instrument hub of claim 9 further comprising a handle connected to the coupling.

14. The surgical instrument hub of claim 9 wherein the lumen extends between the opening at the distal portion and the opening at the proximal portion.

15. The surgical instrument hub of claim 1 wherein the opening in the movable member extends only partially through the movable member.

16. A surgical instrument hub, comprising:
a body having a wall defining a channel for receiving a moving member, the wall defining an aperture positioned proximate an opening defined in the moving member during a portion of the movement of the moving member, the aperture and the opening cooperating to define a valve configured to change a level of fluid communication between the aperture and the opening in the moving member as the moving member moves, edges of the opening and the aperture cutting collected tissue during closing of the valve, the body including a coupling configured to connect the body to a handle.

17. The surgical instrument hub of claim 16 wherein the opening and the aperture selectively overlay each other.

18. The surgical instrument hub of claim 1, wherein a shape of the aperture in the wall is substantially different than a shape of the opening in the moving member.

19. The surgical instrument hub of claim 18, wherein an edge of the aperture in the wall is substantially straight; and
wherein an edge of the opening in the moving member is curved.

20. The surgical instrument hub of claim 1, wherein an edge of the aperture in the wall is sharpened to cut tissue received from the distal portion of the moving member, the edge disposed parallel to a lengthwise axis extending from the proximal portion to the distal portion.

21. The surgical instrument hub of claim 20, wherein rotational movement of the moving member about the lengthwise axis cuts tissue disposed between the aperture and the opening.

22. The surgical instrument hub of claim 1, wherein rotational movement of the moving member about an axis through the distal portion and the proximal portion of the moving member opens and closes the valve.

23. The surgical instrument hub of claim 1, wherein the moving member moves longitudinally along an axis from the distal portion to the proximal portion, movement along the axis opening and closing the valve.

24. The surgical instrument hub of claim 1, wherein the distal portion of the moving member includes a surgical window to cut and receive the tissue; and
wherein a location and timing of opening and closing the valve is varied in relation to the surgical window.

25. The surgical instrument hub of claim 24, wherein movement from the first position to the second position cuts tissue disposed between the opening in the moving member and the aperture in the wall, the tissue being received from a lumen extending between the surgical window and the proximal portion of the moving member.

26. The surgical instrument hub of claim 1, wherein a shape of the aperture in the wall is substantially different than a shape of the opening in the moving member;
wherein an edge of the aperture in the wall is sharpened to cut the tissue received from the distal portion of the moving member, the edge disposed parallel to a lengthwise axis extending from the proximal portion to the distal portion;
wherein the opening in the moving member is curved;
wherein the distal portion of the moving member includes a surgical window to cut and receive the tissue;
wherein a location and timing of opening and closing the valve is varied in relation to the surgical window; and
wherein movement from the first position to the second position cuts tissue disposed between the opening in the moving member and the aperture in the wall, the tissue being received from a lumen extending between the surgical window and the proximal portion of the moving member.

27. The surgical instrument hub of claim 1, wherein the aperture in the wall includes a first edge and a second edge;
wherein the first edge of the aperture in the wall includes a bevel to cut the tissue received from the distal portion of the moving member, a portion of the first edge disposed parallel to a lengthwise axis extending from the proximal portion to the distal portion of the moving member, the first edge cutting received tissue based on a first directional rotation of the moving member about the lengthwise axis; and
wherein the second edge of the aperture in the wall includes a bevel to cut the tissue received from the distal portion of the moving member, a portion of the second edge disposed parallel to the lengthwise axis, the second edge cutting received tissue based on a second directional rotation of the moving member about the lengthwise axis.

* * * * *